(12) United States Patent
Maranghi

(10) Patent No.: US 9,169,586 B2
(45) Date of Patent: Oct. 27, 2015

(54) CHANNELLED NONWOVEN WITH REDUCED SURFACE EXPANSION OF LIQUID FOR THE PRODUCTION OF SANITARY TOWELS AND RELATIVE PROCESS OF MANUFACTURE

(75) Inventor: Marco Maranghi, Prato (IT)

(73) Assignee: FA-MA JERSEY S.P.A., Prato (IT)

( * ) Notice: Subject to any disclaimer, the term of this patent is extended or adjusted under 35 U.S.C. 154(b) by 0 days.

(21) Appl. No.: 13/566,237

(22) Filed: Aug. 3, 2012

(65) Prior Publication Data

US 2014/0039436 A1 Feb. 6, 2014

(51) Int. Cl.

| | |
|---|---|
| *A61F 13/15* | (2006.01) |
| *D04H 18/04* | (2012.01) |
| *D04H 1/425* | (2012.01) |
| *D04H 1/495* | (2012.01) |
| *A61F 13/475* | (2006.01) |
| *A61F 13/511* | (2006.01) |
| *D04H 1/42* | (2012.01) |
| *D04H 1/70* | (2012.01) |
| *D04H 1/49* | (2012.01) |
| *A61F 13/512* | (2006.01) |
| *A61F 13/513* | (2006.01) |

(52) U.S. Cl.
CPC .......... *D04H 18/04* (2013.01); *A61F 13/15731* (2013.01); *A61F 13/4751* (2013.01); *A61F 13/4756* (2013.01); *A61F 13/51108* (2013.01); *D04H 1/425* (2013.01); *D04H 1/495* (2013.01); *A61F 13/15203* (2013.01); *A61F 13/15577* (2013.01); *A61F 13/511* (2013.01); *A61F 13/512* (2013.01); *A61F 2013/15829* (2013.01); *A61F 2013/15983* (2013.01); *A61F 2013/51186* (2013.01); *A61F 2013/51383* (2013.01); *D04H 1/42* (2013.01); *D04H 1/49* (2013.01); *D04H 1/70* (2013.01)

(58) Field of Classification Search
CPC .......... D04H 1/49; D04H 1/70; D04H 1/495; D04H 1/492; D04H 18/04; D04H 1/465; D04H 1/498; D04H 1/42; A61F 13/512; A61F 13/511; A61F 13/15577; A61F 13/15203
USPC ......................................................... 604/372
See application file for complete search history.

(56) References Cited

U.S. PATENT DOCUMENTS 3,485,706 A * 12/1969 Evans ........................... 428/134
5,369,858 A * 12/1994 Gilmore et al. ................. 28/104

(Continued)

FOREIGN PATENT DOCUMENTS

| DE | 103 61 339 A1 | 7/2005 |
|---|---|---|
| GB | 2 114 054 A | 8/1983 |

OTHER PUBLICATIONS

Italian Search Report, dated Jul. 4, 2011, from corresponding Italian application.

*Primary Examiner* — Philip R Wiest
*Assistant Examiner* — Ariana Zimbouski
(74) *Attorney, Agent, or Firm* — Young & Thompson

(57) ABSTRACT

A sanitary towel for physiological liquids includes as topsheet layer a layer of nonwoven cotton (10) having density which varies transversely and provided with a first plurality of longitudinal lines (1) along which the textile has a higher density of fibers with respect to the rest of the textile, each of the longitudinal lines (1) of the first plurality of lines being alternated with a respective longitudinal line (2) of a second plurality of longitudinal lines (2) along which the textile has a lower density of fibers with respect to the longitudinal lines (1).

7 Claims, 8 Drawing Sheets

(56) References Cited

U.S. PATENT DOCUMENTS

| | | | |
|---|---|---|---|
| 2004/0243084 A1* | 12/2004 | Yoshimasa et al. | 604/385.01 |
| 2006/0058762 A1* | 3/2006 | Yang et al. | 604/380 |
| 2007/0207317 A1* | 9/2007 | Willingham et al. | 428/375 |
| 2007/0226970 A1 | 10/2007 | Pourdeyhimi et al. | |
| 2007/0298220 A1* | 12/2007 | Noda et al. | 428/152 |
| 2008/0160859 A1* | 7/2008 | Gupta et al. | 442/364 |
| 2009/0088713 A1* | 4/2009 | Norrby | 604/365 |
| 2010/0324518 A1* | 12/2010 | Naoto et al. | 604/385.02 |

\* cited by examiner

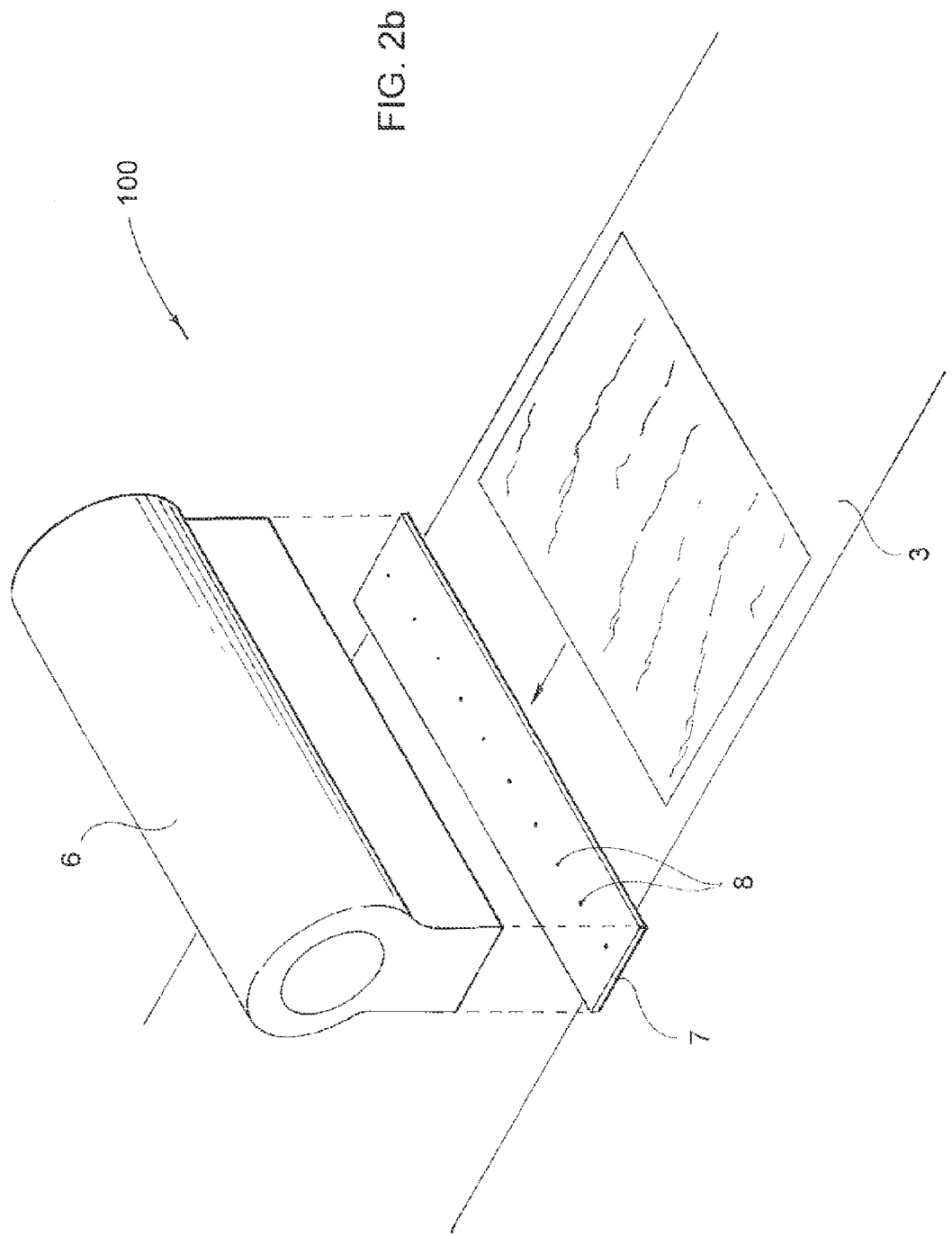

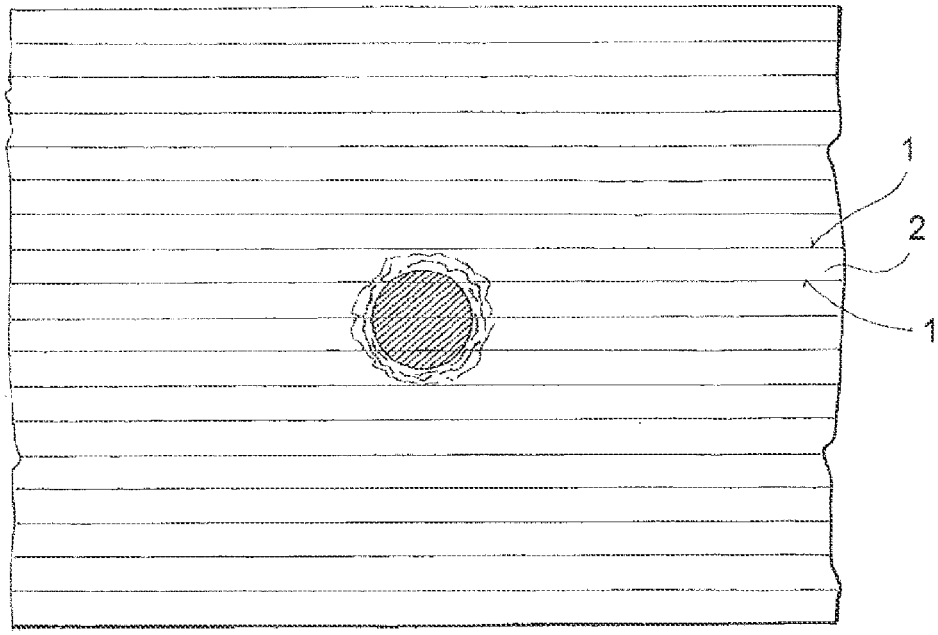
FIG. 3a
FIG. 3b
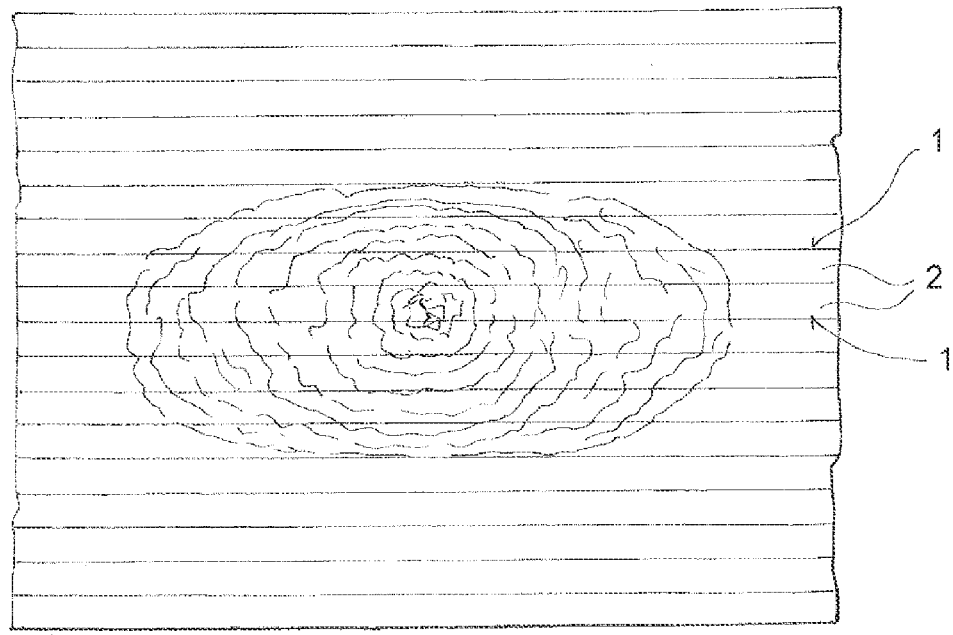

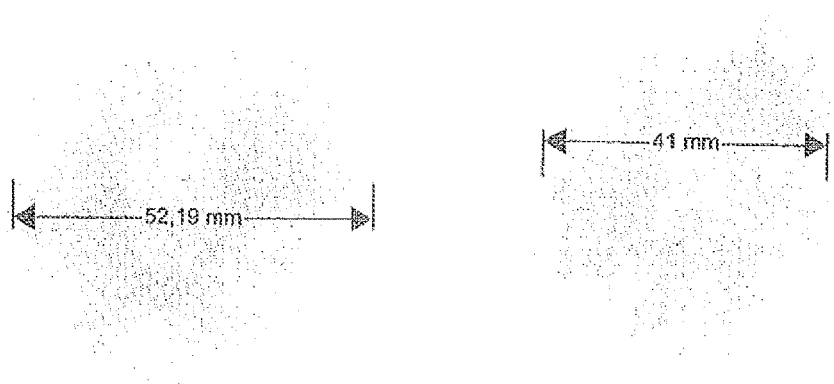
FIG. 4a
FIG. 4b
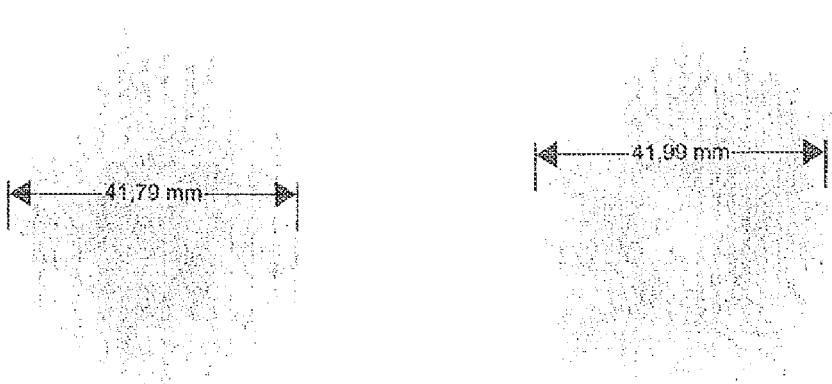
FIG. 4c
FIG. 4d
FIG. 4e

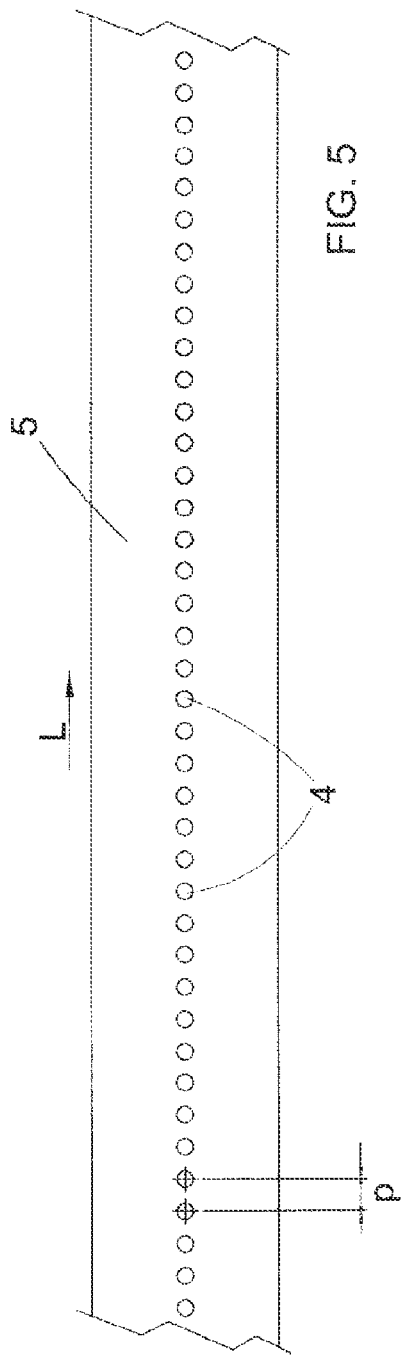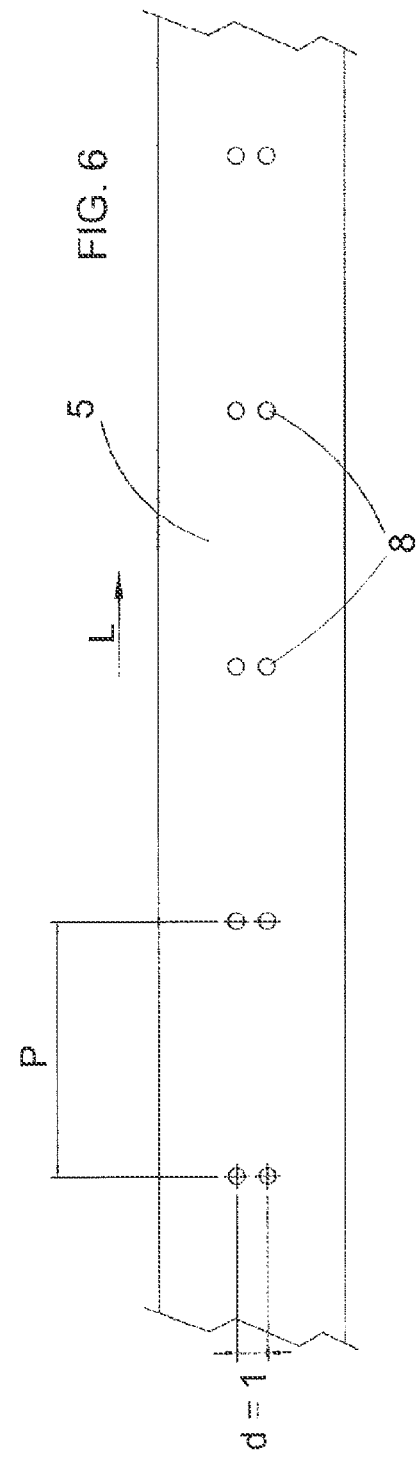

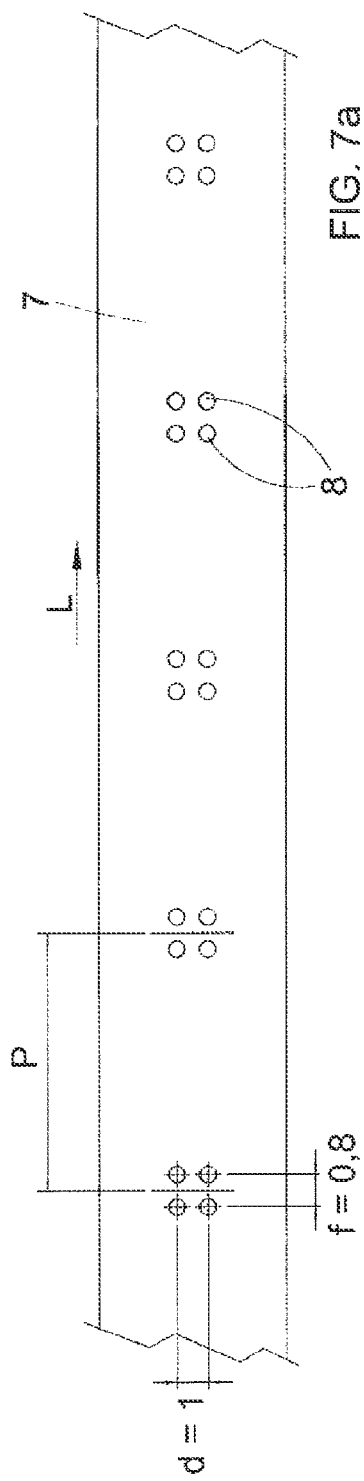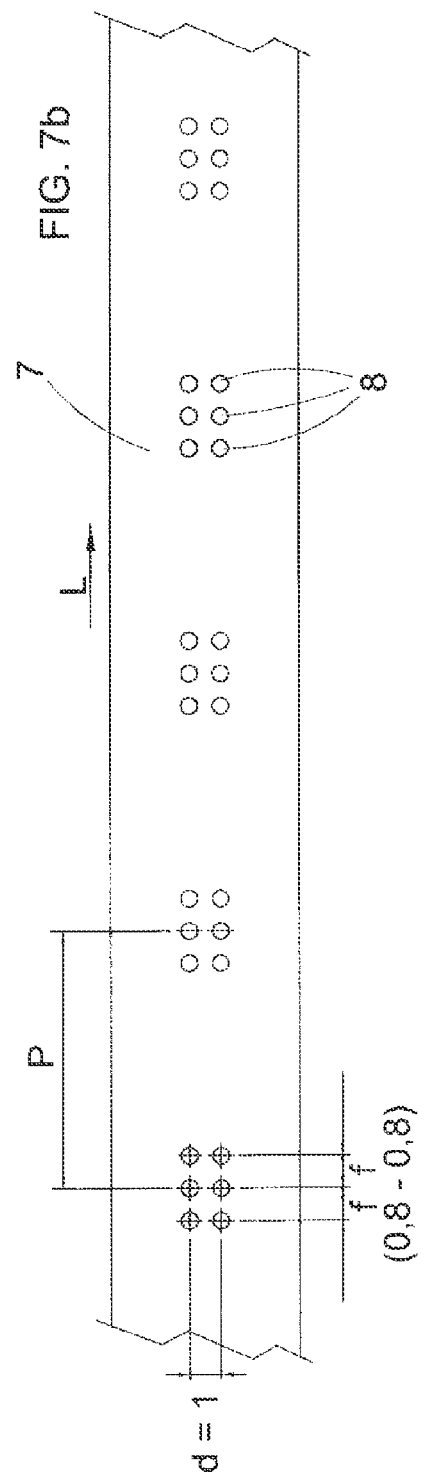

CHANNELLED NONWOVEN WITH REDUCED SURFACE EXPANSION OF LIQUID FOR THE PRODUCTION OF SANITARY TOWELS AND RELATIVE PROCESS OF MANUFACTURE

BACKGROUND OF THE INVENTION

1. Field of the Invention

The present invention relates to sanitary towels for physiological liquids, with high absorbency, provided with a reduced surface expansion of the liquid absorbed through capillarity thanks to the particular manufacture of the surface layer (topsheet) in cotton or similar absorbent materials in natural fibres.

2. Description of the Related Art

Sanitary towels in cotton are more breathable with respect to conventional sanitary towels made with synthetic materials, and therefore generally more comfortable. Moreover these sanitary towels in cotton are suitable for all those who exhibit dermatological problems in contact with synthetic materials.

The sanitary towels in cotton currently present on the market are formed by a thin porous surface layer, in perforated and non-perforated nonwoven cotton, also known as topsheet, which has a function of covering with the sole purpose of forming a hypoallergenic contact layer. Below this topsheet an intermediate absorbent/filtering layer in cotton or in airlaid of cellulose fibres, with greater thickness, is positioned, which forms the core thereof, and a base polymeric film as support, also having the function of providing a surface on which to apply the adhesive strips for the attachment of said sanitary towel to the panty.

These sanitary towels can also be provided with so-called "wings", also adhesive, which ensure an even better attachment of the sanitary towel to the panty. These wings are formed by the topsheet layer supported by the aforementioned polymeric film without any intermediate absorbent layer.

To date this topsheet is obtained from cotton fibres, in the form of a pad, which is subsequently subjected to hydroentangling or water needling (spunlace), thus forming a layer of cotton where the fibres are bound one to the other.

The spunlace technology binds the fibres using jets of water exiting from a jet strip of nozzles at high pressure, in general 60-80 bars, appropriately distanced, for example by 0.8 mm, with a diameter of approximately 0.08 mm. Said jets of water pass through the fibrous pad, binding one to the other the fibres below the high-pressure jets, and the nonwoven obtained in this way is resistant and at the same time soft, with grams per square meter varying generally from 20 to 60 g/m$^2$.

Since cotton is notoriously an absorbent material with high capillarity, this type of sanitary towel suffers the disadvantage of exhibiting a high expansion of the liquid which traverses it with the consequent disadvantage of having a widening of the stain of liquid as far as the wings, soiling them.

SUMMARY OF THE INVENTION

The object of the present invention is to provide a sanitary towel able to overcome, at least in part, the disadvantages suffered by the prior art, in particular a sanitary towel in cotton having a reduced surface expansion of the liquid absorbed, in particular on the wings, ensuring at the same time a high absorbency of liquid.

A further object is that of providing such a sanitary towel which can be made with a simple and economical process, easy to perform.

These objects are achieved by the sanitary towel with wings in absorbent material of natural fibres such as cotton or viscose, with microperforations or plain.

The object of the present invention is a sanitary towel with wings comprising as surface layer or topsheet a layer of absorbent material in natural fibres such as cotton and/or any other natural fibre and mixtures thereof with viscose or polylactic acid or another fibre suitable for the purpose, in the form of nonwoven textile, said topsheet having a density which varies transversely and is provided with a first plurality of longitudinal lines (grooves) along which said textile has a higher density of fibres with respect to the rest of the textile, each one of said lines of said first plurality of lines being alternated with a respective longitudinal line of a second plurality of lines along which said textile has a lower density of fibres.

The higher density of fibres along the first plurality of lines is due to the fact that the fibres there are more compressed and the textile has a smaller thickness: this means that the capillarity due to the greater closeness between fibre and fibre tends to increase in the longitudinal direction creating lines or bands of channelling for the liquid.

The lower density of fibres along each line of said second plurality of lines is due to the fact that the fibres there are less compressed and more distanced one from the other: this means that the transfer of liquid from one fibrella (fibre) to the other is more difficult, slowing down the flow of the capillarity in the transverse direction.

In practice the longitudinal lines with lower density represent lines of barrier to the flow of the liquid in a transverse direction (perpendicular to these lines) coming from the adjacent lines with higher density, facilitating therefore the channelling of the liquid along the lines with higher density (and high absorbency).

The specific alternation of lines with different density of fibres is obtained by means of a specific process of preparation of the nonwoven textile which forms the topsheet which will now be described.

This process comprises:
a first step (a) of hydroentangling with water of a layer of fibres with jets of water adjacent one to the other, suitable for applying pressures lower than or equal to 60 bars to said layer, in order to obtain a light cohesion between the fibres, and
a second step (b) of hydroentangling with water of the hydroentangled pad obtained from the first step (a), using jets of water with pressures higher than or equal to 100 bars or with higher flow rate with respect to step (a), appropriately distanced one from the other, with a pitch (along the transverse line L of the topsheet of FIG. 1a) of at least 0.5 mm one from the other, preferably of at least 1 mm, more preferably of at least 2 mm.

The jets of water at high pressure or with higher flow rate of step (b) mean that the innermost fibres of the topsheet layer are also cohered, which does not occur in the first step where the pressures are low and the binding is superficial.

The jets of water at high pressure or with higher flow rate of step (b) are generally more distanced one from the other and with a greater nozzle diameter with respect to the jets of water with low pressure or with lower flow rate of step (a): in this way the jets of water at high pressure once again go to hit only a part of the zones previously hit by the jets at lower pressure, therefore creating a textile with more compressed zones (of high density) alternated with less compressed zones (of lower density).

Steps (a) and (b) are applied on the same side 30 of the topsheet (FIG. 1*b*). Said steps can be performed in a single phase using at the same time jets of water both with high and low pressure by means of the simultaneous use of different nozzles, with different diameter, as will subsequently be described in detail.

The layer of fibres to be subjected to step (a) can be pre-needled, needle-punched in the form of a pad or also only be constituted by a plurality of folded or carded webs.

The treatment with jets of water used in steps (a) and (b) of the present process is a technology known in the art and also referred to as water binding (also referred to as spunlacing, hydroentangling, etc.). Refer for example to U.S. Pat. No. 3,485,706 or what is described in the patent application EP 1359241 incorporated here in full for reference.

In the art entangling is generally performed at pressures generally around 60-80 bars, using nozzles of small diameter, for example 0.08 mm, placed almost in contact one with the other, therefore with a different arrangement with respect to step b).

BRIEF DESCRIPTION OF THE DRAWING FIGURES

Reference will now be made to the accompanying drawings which are purely an example, and therefore non-limiting, of embodiments of the present invention, in which:

FIG. 1*a* is an enlarged view from above, and partially interrupted transversely, of a topsheet in accordance with the present invention;

FIG. 1*b* is a sectioned view, enlarged, of the topsheet of FIG. 1*a* taken along line I-I;

FIGS. 2*a*-2*b* are schematic perspective views of the unit of hydroentangling in two different phases of preparation of the topsheet of the present invention;

FIGS. 3*a*-3*b* are views from above of the topsheet of the invention respectively at the moment of formation of the stain of liquid and in a subsequent moment of expansion of said stain;

FIGS. 4*a*)-*e*) are views from above of a conventional topsheet a), in microperforated 35 g/m$^2$ cotton and of some topsheets b)-e) of the invention, in microperforated 35 g/m$^2$ cotton, after a predetermined time from the addition of test liquid;

FIG. 5 is a view from above, enlarged and partially interrupted, of an arrangement of low-pressure nozzles in the respective nozzle-holder jet strip;

FIG. 6 is a view from above, enlarged and partially interrupted, of an arrangement of high-pressure nozzles in the respective nozzle-holder jet strip;

Figure 8:
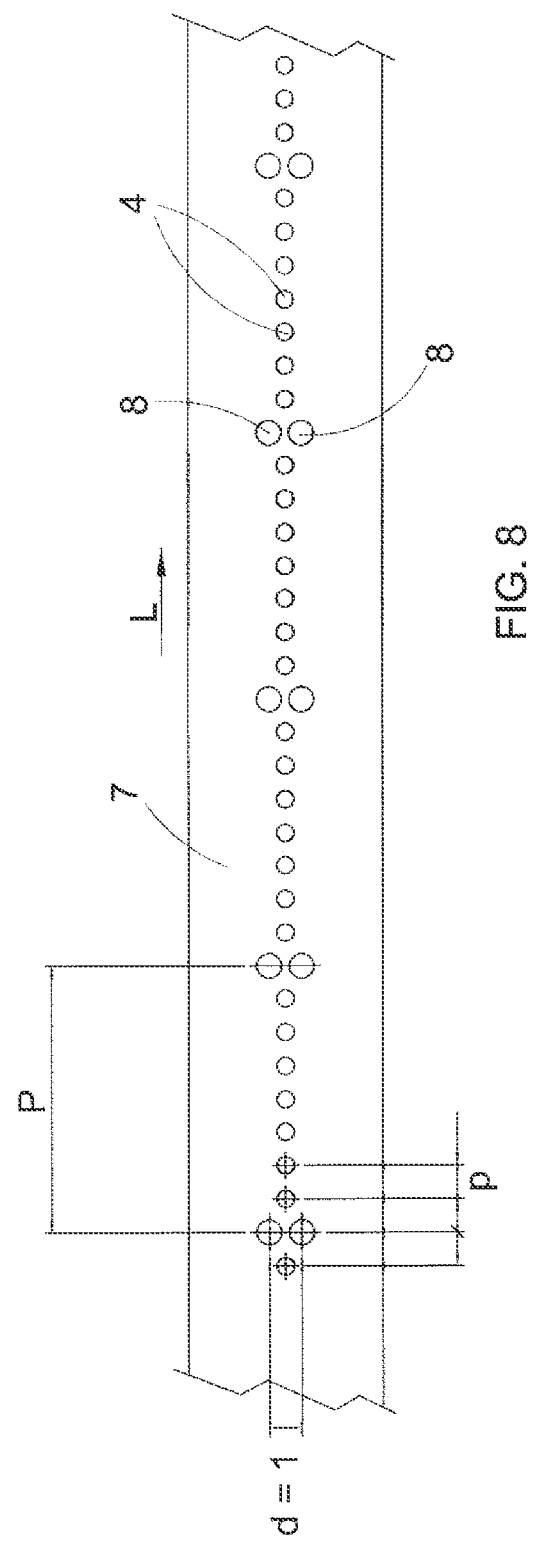

FIGS. 7*a*)-*b*) is a view from above, enlarged and partially interrupted, of two different arrangements of high-pressure nozzles in the respective nozzle-holder jet strip;

FIG. 8 is a view from above, enlarged and partially interrupted, of a single arrangement of high-pressure and low-pressure nozzles in a single nozzle-holder jet strip.

DETAILED DESCRIPTION OF THE INVENTION

Figure 1A:
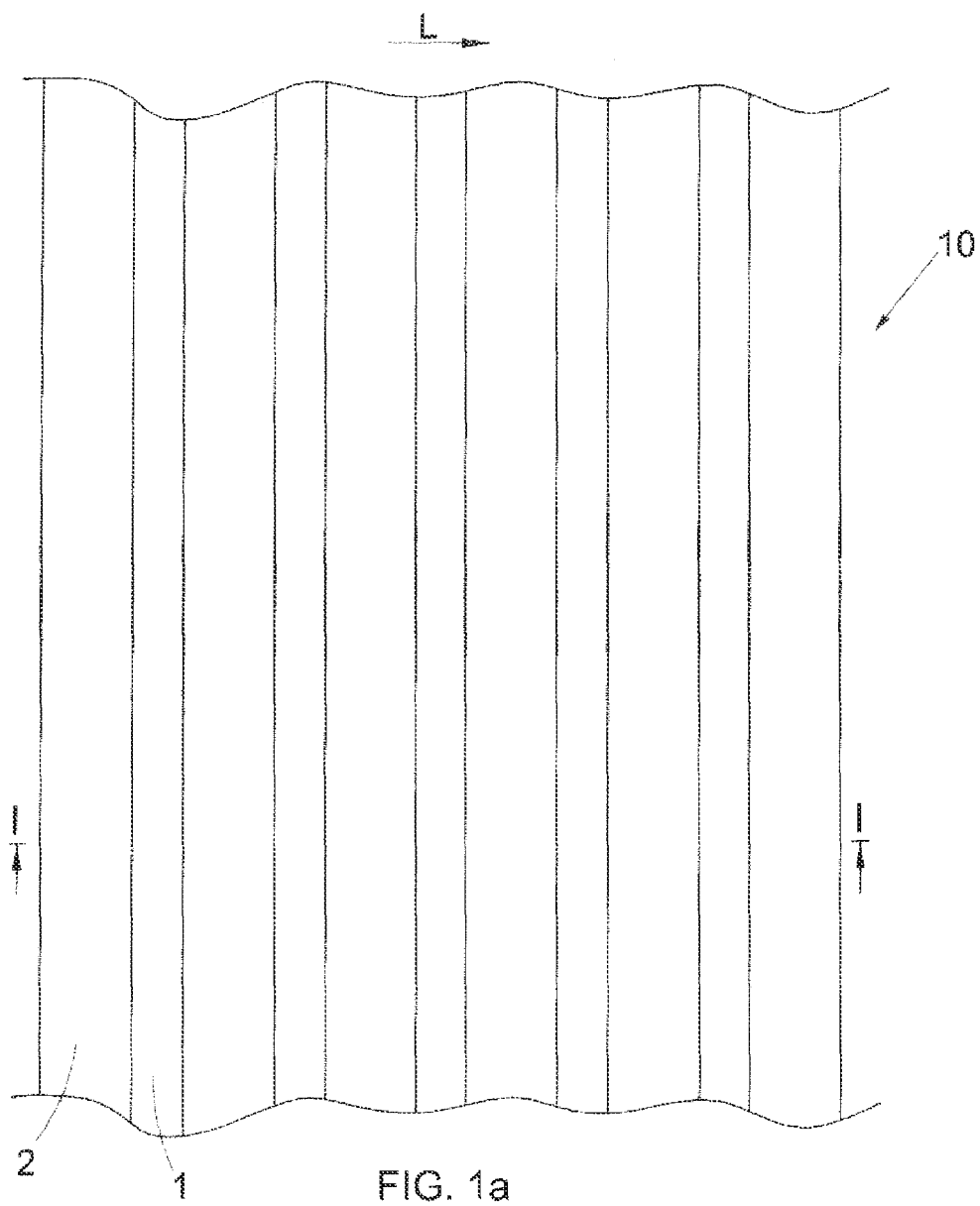
Figure 1B:
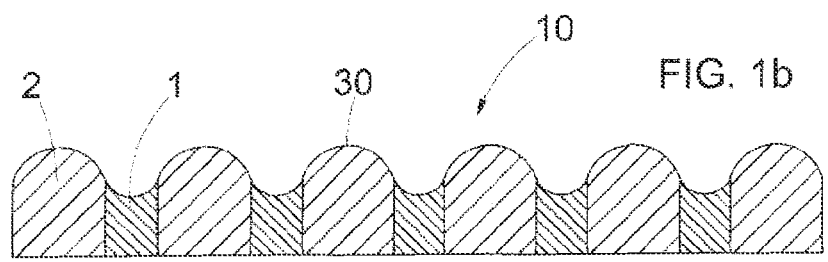

As illustrated in FIGS. 1*a* and 1*b*, the topsheet layer 10 in accordance with the present invention is a layer provided with a first plurality of longitudinal lines 1, along which the fibres are more compressed (higher density of fibres and smaller thickness), and of a second plurality of longitudinal lines 2, alternated with the longitudinal lines 1, along which the fibres are less compressed (lower density of fibres and greater thickness).

Figure 2A:
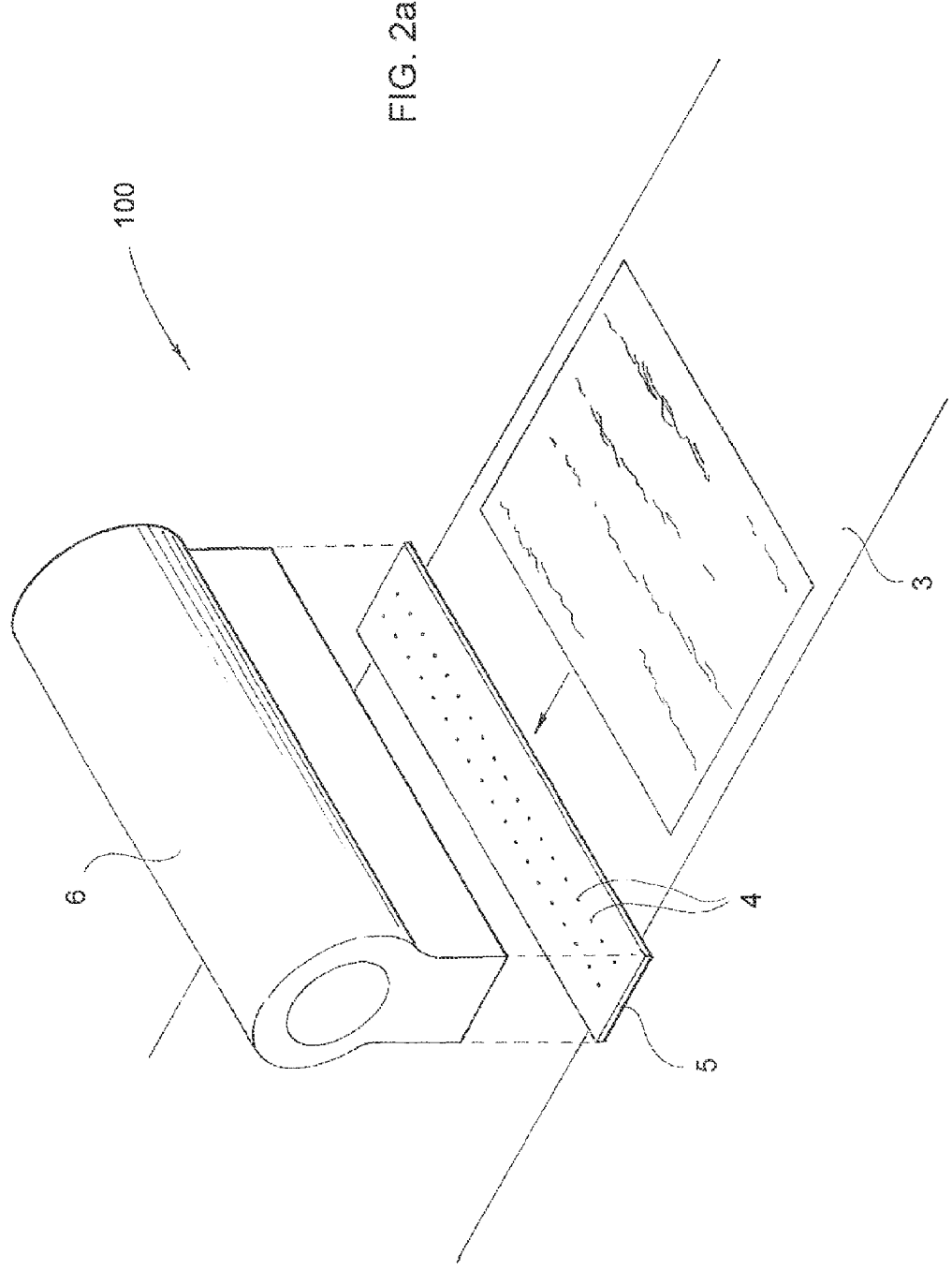

Referring to FIGS. 2*a*-2*b*, the topsheet 10 in nonwoven cotton is prepared according to the following method: the starting layer which will go to form the topsheet is a layer of fibres coming generally from a carding plant, also known as "web", which is placed on a conveyor belt 3 which supplies the hydroentangling section 100.

In said section 100 the fibres of said layer (web) are subjected to a first phase of entangling with water by means of pressurised jets which allow the fibres to cohere one with the other: this is necessary in that in the web coming from the carding plant the fibres are only joined through reciprocal adhesion but break and separate if subjected to traction.

Referring to FIGS. 2*b*) and 5, in this first phase of hydroentangling a plurality of nozzles 4 with diameter ($\Phi$) of approximately 0.08 mm and a distance between nozzle and nozzle (pitch, p) (along the transverse line L in FIG. 5) equal to approximately 0.8 mm are used. These nozzles 4 are holes formed in a steel plate 5 which acts as jet strip, and can be arranged in a single row (FIG. 5) or in several rows, for example two (FIG. 2*a*) appropriately distanced one from the other.

Other examples of diameter ($\Phi$) of nozzle 4 are 0.06 mm and 0.10 mm.

In one embodiment said rectangular jet strip 5 generally has a width of 20-25 mm, thickness of approximately 0.5 mm and length of approximately 2.5 m, and is perforated to a design with holes of different pitch and diameter according to the type of binding which is to be performed and of average grams per square meter value which is required for the topsheet 10.

The abovementioned dimensions of the jet strip 5 are not binding for the purpose of the present invention and can also vary by a few centimeters up to even ⅗ meters according to the size of the type of machine on which it is to be mounted.

Said jet strip 5 is mounted on a nozzle-holder injector 6 which acts as distributor of the flow of water, which is placed, in fixed position, above the conveyor belt 3 which makes the material advance in the direction of the arrow indicated in FIG. 2*a*. Said distributor 6 goes to supply with water the plate 5 wherein the holes of the nozzles 4 have been formed.

In this first step a) water is used at a pressure which is not high, generally between 30 and 40 bars, up to even approximately 60 bars.

The entangled layer of fibres obtained in said first step (a) is then passed to a zone where part of the water absorbed can be discharged, and subsequently sent again into the entangling unit where the first jet strip 5 has been replaced with a second jet strip 7 (FIGS. 2*b*, 6, 7*a*), 7*b*)) suitable for supporting nozzles 8 with greater diameter with respect to the previous nozzles 4 and distanced one from the other with a greater pitch (P), (along the transverse line L in FIG. 6).

By way of an example the nozzles 8 for high pressure can have a diameter ($\Phi$) of 0.8 mm or of 0.12 mm, 0.14 mm, 0.16 mm, and can be distanced with a pitch (P) which varies from 1 mm up to 5 mm, preferably 2-3 mm. Said nozzles 8 can also be arranged in several horizontal rows.

FIGS. 6, 7*a*), 7*b*) illustrate different arrangements of high-pressure nozzles 8 in the same number of nozzle-holder jet strips 7.

FIG. 6 shows a first embodiment of the jet strip 7 containing nozzles 8 with diameter of 0.12 mm, which are arranged at a distance P of 2 or 3 mm one from the other. The nozzles 8 are also arranged in two horizontal rows (along the line L), which have a distance (d), one from the other, of approximately 1 mm.

FIG. 7a shows a second embodiment of the jet strip 7 containing nozzles 8 with diameter of 0.12 mm, arranged in two rows which have a distance (d), one from the other, of approximately 1 mm.

Next to each nozzle 8 of each row a second nozzle 8 is positioned, at a distance (f) for example of approximately 0.8 mm. In this way groups of nozzles 8 are formed along the line L, each one formed by four nozzles 8 practically adjacent one to the other. Each group is distant one from the other by a pitch (P) which can be equal to 2, 3, 5 mm.

FIG. 7b shows a third embodiment of the jet strip 7 containing nozzles 8 with diameter of 0.12 mm, arranged in two rows which have a distance (d), one from the other, of approximately 1 mm.

Next to each nozzle 8 of each row two other nozzles 8 are positioned, at a distance (f) for example of approximately 0.8 mm. In this way groups of nozzles 8 are formed, each one formed by six nozzles 8. Each group is distant one from the other by a pitch (P), along the line L, which can be equal to 2, 3, 5 mm.

In the embodiments of FIGS. 6, 7a), 7b) the distance f between the high-pressure nozzles 8, positioned one alongside the other, can also be equal to 0.6 mm rather than 0.8 mm.

The abovementioned dimensions of the jet strip 7 are not binding for the purpose of the present invention and can also vary by a few centimeters up to even ⅗ meters according to the size of the type of machine on which it is to be mounted.

Both jet strips 5 and 7 are positioned in a transverse direction to the movement of the conveyor belt 3, as shown in FIGS. 2a and 2b with the arrow, in such a way that, when the belt 3 moves, the jets of water exiting from the nozzles 4 and 8 hit the entire pad of fibres along longitudinal lines. The dimensions of these jet strips 5 and 7 can be for example 2 m in length and 25 cm in width.

In practice the hydroentangling at higher pressures, generally higher than 100 bars, or with higher flow rates with respect to the first entangling (a), takes place only in specific points or zones (longitudinal lines 1) of the topsheet thanks to the arrangement of the nozzles 8 in the jet strip 7: for this reason the density in said longitudinal lines 1 is higher with respect to the zones (longitudinal lines 2) not hit by the high-pressure jets.

Through the nozzle-holder device 6 and the alternation of nozzles 4 and 8 which operate at different pressures, different pressures are applied along the longitudinal lines of the nozzles: said lines represent lines (or rows) of sealing (bonding) along which the surface fibres bind more or less with the underlying fibres according to the pressure used.

Subsequently the topsheet obtained from said second step (b) is air-dried and wound on a reel.

As mentioned above, it is also possible for said steps (a) and (b) to be performed at the same time in a single phase using jets of water which hit the pad with different flow rates and therefore with different hydraulic powers, by means of a single jet strip 7 where both types of nozzles 4 and 8 are arranged, as illustrated in FIG. 8.

In fact, considering a jet strip 7 of the type of FIG. 8 with holes of different diameter, for example 0.08 mm 0.12 mm, with the same pressure a greater hydraulic energy of approximately double the power will be obtained for the holes with larger diameter, in that the expression of the power on the diameter of the holes is squared.

For example with 1000 holes with diameter of 0.08 mm at the pressure of 100 bars a flow rate of 361 l/h is obtained; the same 1000 holes with diameter of 0.12 mm at the same pressure of 100 bars will have a flow rate of 811 l/h: an increase of 125% of hydraulic energy.

In practice, using the same pressure yet a single jet strip with two different types of holes, the same effect obtained at the end of step b) is achieved.

In said embodiment referred to FIG. 8, the nozzles for low pressure 4 have a diameter ($\Phi$) of approximately 0.08 mm and a distance between nozzle and nozzle (p) equal to approximately 0.8 mm and are only placed along a single row, while the nozzles 8 of diameter of 0.12 mm and are placed in two rows which have a distance (d), one from the other, of approximately 1 mm, each nozzle 8 being placed at a pitch P one from the other, along the line L, which can be equal to 2, 3, 5 mm.

In practice, using the same pressure yet utilising simultaneously nozzles 4 at low pressure/flow rate and nozzles 8 at high pressure/flow rate we have greater binding effect with the holes 8 of larger diameter for greater hydraulic power of the flow of water due to a greater passage: a greater and more extended barrier effect with a greater longitudinal capillarity due to the greater vicinity of the large holes 8;

lower binding effect with the holes 4 of smaller diameter, in the drawing with diameter 0.08: the holes 4 with smaller diameter have a lower flow rate of the water and therefore a lower hydroentangling energy.

Nevertheless the embodiments of jet strip 7 illustrated in FIGS. 7a and 7b are preferred, where at each pitch P there is a group of nozzles 8 placed very close one to the other.

In fact, using a jet strip 7 where the larger holes 8 are arranged in several horizontal rows and form groups, and where each group is distanced from the other by a pitch P, there will be a greater density of holes per cm with respect to the configuration in a single row.

In this configuration with groups the distance of the holes 8, inside the group, is an important process parameter: in fact the holes 8 with pitch 0.8 mm will have a density of holes of 12.5 holes per cm, while the holes 8 with pitch 1.0 mm will have a density of 10 holes per cm.

As illustrated in FIGS. 3a and 3b, while the lines with lower density 2 represent longitudinal channellings for the liquid along which it can expand, the lines with greater density 1 constitute a barrier to the passage of the liquid in transverse direction with respect to said longitudinal lines 2.

The Applicant has surprisingly found by means of tests that the transverse expansion of liquid is considerably reduced when a natural nonwoven absorbent material such as cotton is subjected to the process of the present invention.

In fact, as shown in FIGS. 4a)-e), the transverse diffusion of the stain is reduced a great deal by changing from a conventional topsheet (FIG. 4a)) to topsheets made according to the invention (FIGS. 4b)-e)).

Moreover the topsheet of FIGS. 4b)-d) in accordance with the invention show a diffusion of liquid substantially similar one to the other: said topsheets were obtained by using the jet strip 7 of FIG. 6 respectively with pitch P=3 mm, P=3 mm and P=2 mm.

The topsheet of FIG. 4e) in accordance with the invention, which shows the smaller transverse diffusion of liquid, was obtained by using the jet strip 7 of FIG. 7 with a pitch (P) equal to 5 mm.

Without wishing to be bound to any theory, it can be presumed that the wider the areas with higher density and binding 1 (made with several nozzles 8 adjacent one to the other), the greater the orientation of the capillarity in a longitudinal rather than a transverse direction. This prevents the fluid from diffusing through transverse capillarity to the sides of the topsheet, and therefore towards the wings of the sanitary towel, with considerable advantages.

This is illustrated schematically in FIGS. 4a)-e) which show the stains on various topsheet samples after a predetermined time from the addition of an appropriate test liquid which simulates the behaviour of blood: in FIG. 4a) the conventional topsheet, in microperforated 35 g/m² cotton, hydroentangled at a single pressure of 60-80 bars with nozzles of the same diameter, has a stain with width much greater with respect to some topsheets b)-e) of the invention, in microperforated 35 g/m² cotton.

The cotton fibres used for the formation of the topsheet can be of any micronaire, for example 2 to 5, or can be a mixture of fibres with different micronaire.

Similarly to the above, in the case of a natural fibre different from cotton or in the case of mixtures of fibres of cotton, viscose, polylactic acid (PLA) or other similar fibres, the fibres used can be of any dimensions.

With the present process it is possible to obtain a topsheet with a conventional grams per square meter value where the weight is constant over the entire surface yet the density and the thickness are different according to whether in a zone of high density along the longitudinal lines 1 or in a zone with low density along the longitudinal lines 2.

In practice these zones along the longitudinal lines 1 create a transverse barrier effect and diffuse the fluid longitudinally: the greater the density differential between the lines 1 and the lines 2, the greater the channelling of the flows longitudinally.

Therefore the greater or smaller difference in density (g/cm³) between said first plurality of longitudinal lines 1 and said second plurality of lines 2 is to be chosen on the basis of the end use of the topsheet.

In general, in order to obtain good channelling, the difference in density is at least 5%, preferably at least 10%, more preferably around 15-20%, even if these values are not binding for the purpose of the present invention.

Using the nozzles 8 described in FIG. 7a with a pitch P of 3 mm for each group of nozzles, a topsheet sample was obtained, provided with a density differential equal to approximately 15% which exhibited good longitudinal channelling of the flow.

More particularly the density obtained on 35 g of cotton using nozzles 4 as in FIG. 5 with pressure at 60 bars, and nozzles 8 as in FIG. 7a with pressure at 100 bars, a density of 0.095 g/cm³ was obtained in the zones with high density (longitudinal lines 1) shown in FIG. 1a, and a density of 0.082 g/cm³ in the zones with low density (longitudinal lines 2), resulting in a density differential equal to 16% approximately.

In practice the Applicant, by means of tests, has noted that the transverse diffusion of the liquid appears to be further reduced when, in addition to a greater differentiation of density, there is also a greatest width possible of the zones with low density and the zones with high density, and/or a greater number of zones with high and low density in a transverse direction.

In fact the Applicant has observed that the greater the difference of density between the zones with high and low density, the greater the channelling of the fluids in the longitudinal direction;

the greater the width of the zones (lines) with low and high density, the greater the barrier effect which is obtained;

the greater the number of the zones (lines) with low and high density per linear centimeter in transverse direction, the greater the barrier effect.

Numerous detail variations and changes can be made to the present embodiment of the invention, within the reach of a person skilled in the art and in any case coming within the scope of the invention.

The invention claimed is:

1. A process for preparing an absorbent topsheet layer having a density which varies in the transverse direction for reduced transverse capillarity, the absorbent topsheet layer configured for a cotton-based sanitary towel with wings for physiological liquids, said process comprising: (a) a first hydroentangling of a pre-needled or pre-punched layer of fibres with pressures between 30 and 60 bars, with jets of water adjacent one to the other, in order to obtain a light cohesion between the fibres resulting in a lightly hydroentangled pad; and (b) a second hydroentangling of the lightly hydroentangled pad obtained from step (a), using pressures higher than or equal to 100 bars, said jets being distanced one from the other with a pitch of at least 0.5 mm; wherein said topsheet layer consists of a nonwoven form of natural fibres of cotton or a mixture thereof with polylactic acid and/or viscose, and said process provides the topsheet layer with a first plurality of longitudinal straight lines with a form of grooves having a density of fibres of at least 5% greater than a second plurality of longitudinal straight lines, each alternated with each longitudinal line, said lines with lower density representing longitudinal channelings for the liquid along which the liquid can expand, the lines with greater density constituting a barrier to the passage of the liquid in the transverse direction with respect to said longitudinal lines, and said first plurality of longitudinal lines of higher density of fibres having a smaller thickness with respect to the thickness of said second plurality of longitudinal lines.

2. The process according to claim 1 wherein the layer of fibres to be used in step (a) is fed on a conveyor belt coming from a carding unit.

3. The process according to claim 1 wherein the nozzles for the water jets used in step (a) have a diameter ($\Phi$) of approximately 0.08 mm, are mounted on a first rectangular jet strip placed over the conveyor belt and are distanced one from the other by a distance (pitch, d) equal to approximately 0.8 mm.

4. The process according to claim 1 wherein the nozzles to be used in step (b) have a diameter comprised between 0.8 mm and 0.12 mm ($\Phi$), are mounted on a second jet strip and are distanced one from the other by a pitch (P) comprised between 1 mm and 5 mm, each of said nozzles also being possibly adjacent to one or more nozzles at each pitch (P).

5. The process according to claim 4 wherein the nozzles in the jet strip are placed in several horizontal rows at a distance (d) one from the other, each nozzle of each row being adjacent to one or more nozzles at a distance (f) one from the other so as to form groups of nozzles, each group being distant from the other by a pitch (P) which varies from 1 mm to 5 mm.

6. The process according to claim 1 wherein the first plurality of longitudinal lines having a higher density of fibres is obtained at the end of step b) and the second plurality of longitudinal lines having a lower density of fibres is obtained at the end of step a).

7. The process according to claim 1, wherein transverse diffusion of liquid ranges from 35.39 mm to 41.99 mm.

* * * * *